United States Patent
Zhou et al.

(10) Patent No.: US 10,258,699 B2
(45) Date of Patent: Apr. 16, 2019

(54) ANGIOPEP AND DERIVATIVES THEREOF FOR IMAGING AMYLOIDS

(71) Applicant: University Of Science And Technology Of China, Hefei, Anhui (CN)

(72) Inventors: Jiangning Zhou, Anhui (CN); Chenwei Wang, Anhui (CN); Doudou Nan, Anhui (CN); Xinmeng Wang, Anhui (CN)

(73) Assignee: University Of Science and Technology of China, Hefei, Anhui (CN)

( * ) Notice: Subject to any disclaimer, the term of this patent is extended or adjusted under 35 U.S.C. 154(b) by 0 days.

(21) Appl. No.: 15/520,516

(22) PCT Filed: Oct. 24, 2014

(86) PCT No.: PCT/CN2014/089371
§ 371 (c)(1),
(2) Date: Apr. 20, 2017

(87) PCT Pub. No.: WO2016/061801
PCT Pub. Date: Apr. 28, 2016

(65) Prior Publication Data
US 2017/0304469 A1    Oct. 26, 2017

(51) Int. Cl.
| | | |
|---|---|---|
| *A61K 51/00* | (2006.01) | |
| *A61M 36/14* | (2006.01) | |
| *A61K 49/00* | (2006.01) | |
| *A61K 51/08* | (2006.01) | |

(52) U.S. Cl.
CPC ...... *A61K 49/0056* (2013.01); *A61K 49/0032* (2013.01); *A61K 49/0043* (2013.01); *A61K 51/088* (2013.01)

(58) Field of Classification Search
CPC .............. A61K 49/00; A61K 49/0032; A61K 49/0043; A61K 49/0056; A61K 51/00; A61K 51/08; A61K 51/088
USPC .......... 424/1.11, 1.49, 1.65, 1.69, 1.81, 1.85, 424/1.89, 9.1, 9.2, 9.3, 9.4, 9.5, 9.6; 514/1.1, 13.3, 21.4; 530/300, 316, 326
See application file for complete search history.

(56) References Cited

U.S. PATENT DOCUMENTS 8,877,197 B2 *  11/2014  Van Vlasselaer ...... C07K 16/40
                                                            424/130.1

FOREIGN PATENT DOCUMENTS

| CN | 101160403 A | 4/2008 |
|---|---|---|
| CN | 102510759 A | 6/2012 |
| CN | 102775472 A | 11/2012 |
| EP | 2260874 A1 | 12/2010 |
| EP | 2360258 A2 | 8/2011 |
| WO | WO-2010121379 A1 | 10/2010 |

OTHER PUBLICATIONS

"International Application No. PCT/CN2014/089371, International Search Report dated Jul. 22, 2015", (Jul. 22, 2015), 3 pgs.
"International Application No. PCT/CN2014/089371, Written Opinion Report dated Jul. 22, 2015", (Jul. 22, 2015), 3 pgs.
"European Application Serial No. 14904354.9, Extended European Search Report dated Jun. 13, 2018", 10 pgs.
Demeule, Michel, et al., "Identification and Design of Peptides as a New Drug Delivery System for the Brain", The Journal of Pharmacology and Experimental Therapeutics vol. 324 No. 3 XP008095811, (2008), 10 pgs.
Ke, Weilun, et al., "Gene delivery targeted to the brain using an Angiopep-conjugated polyethyleneglycol-modified polyamidoamine dendrimer", Biomaterials30, (2009), 6976-6985.

* cited by examiner

*Primary Examiner* — D. L. Jones
(74) *Attorney, Agent, or Firm* — Schwegman Lundberg & Woessner, P.A.

(57) ABSTRACT

The present application relates to the molecular labeling and in vivo imaging of amyloids. Specifically, the present application relates to a polypeptide-based method/vector for targeting amyloids. Such a method/vector enables the transportation of compounds or drugs across blood-brain-barrier of an individual and then binding to amyloids in brain. Particularly, the vector of the present application can transport an imaging group linked to the vector across the blood-brain-barrier, and can binds to amyloids in brain, and thus enables the labeling and imaging of amyloid deposits. When used as an imaging agent for detecting amyloid deposits in body or tissues, the vector may be labeled with suitable optical imaging groups, radioactive isotopes or imaging groups suitable for MRI or CT detection. The method/vector can especially used for the in vivo non-invasive diagnosis of amyloid-related diseases including Alzheimer's disease, and for the observation of the therapeutic effect of drugs targeting amyloid deposits.

4 Claims, 6 Drawing Sheets
Specification includes a Sequence Listing.

SEQUENCE LISTING

```
<160> NUMBER OF SEQ ID NOS: 1

<210> SEQ ID NO 1
<211> LENGTH: 19
<212> TYPE: PRT
<213> ORGANISM: Homo sapiens

<400> SEQUENCE: 1

Thr Phe Phe Tyr Gly Gly Ser Arg Gly Lys Arg Asn Asn Phe Lys Thr
1               5                   10                  15

Glu Glu Tyr
```

ANGIOPEP AND DERIVATIVES THEREOF FOR IMAGING AMYLOIDS

PRIORITY APPLICATIONS

This application is a U.S. National Stage Filing under 35 U.S.C. 371 from International Application No. PCT/CN2014/089371, filed on 24 Oct. 2014, and published as WO2016/061801 on 28 Apr. 2016; which application and publication are incorporated herein by reference in its entirety.

FIELD

The present application relates to novel use of a polypeptide and the derivatives thereof, and to a method for the imaging and diagnosis of related diseases using optical imaging etc.

BACKGROUND

Alzheimer's Disease (AD) is a neurodegenerative disease which has a hidden onset and deteriorates progressively. In clinical, AD is mainly characterized by Cognitive decline, irreversible memory impairment, orientating ability disorder, language dysfunction, and the like. Brain tissue autopsy showed a large amount of senile plaques (SPs) formed by the aggregation of amyloid-β (Aβ) peptides and many neurofibrillary tangles (NFTs) formed by the filaments of highly phosphorylated tau proteins, and the lost of neurons and synapses. The amyloid deposits mentioned in the present application include, but not limited to, senile plaques.

Senile plaques formed by the amyloid deposit, which are one of the markers of AD, are used as the gold standard in the diagnosis of AD by autopsy or biopsy clinically. Recently, methods for the detection of the amyloid deposition mainly include biopsy and histological analysis of autopsy materials. Both of these two methods have obvious defects: biopsy results in relatively big trauma and has a risk, while autopsy can only be used for post mortal diagnosis. Thus, a simple, effective, and non-aggressive method for detecting and quantifying amyloid deposits in a patient's brain will be very useful for the diagnosis and treatment of related diseases, especially AD.

As amyloid deposits in brain have many same physical properties as the normal brain tissues (e.g., density and water content), it is difficult to directly image these deposits in vivo. Attempts have previously been performed to use magnetic resonance imaging (MRI) and computed tomography (CT) for the direct (without using developing agent) imaging of amyloid deposits. However, the effects of these attempts are not satisfying or amyloid deposits can only be detected under certain advantageous conditions.

Typical fluorescent dyes, such as Congo Red (CR), Thioflavin S (ThS), and Thioflavin T (ThT), are able to highly specifically bind to amyloid deposits (senile plaques) in vitro. These ligands with high affinity can be modified and labeled with positron radioactive isotopes. As a method mostly investigated recently, positron emission tomography can be used to visibly detect the distribution and amount of senile plaques in AD patients in vivo if the labeled ligands can successfully enter into brain tissues. These PET imaging agents can improve accuracy of diagnosis, provide direct estimation for the study and treatment with anti-Aβ drugs, and thus enable the diagnosis at an early stage.

The ligands used for the detection of amyloid deposits in a living brain must be able to pass through blood-brain-barrier (BBB). Congo Red, Thioflavin S, and Thioflavin T etc. can not pass through Blood-brain-barrier for their relatively bigger molecular size and charge. Ligands having a relatively smaller molecular size (compared with Congo Red) can be used to improve brain intake and increase lipophilicity. Recently, potent ligands (most of which are obtained by modification on the basis of the structures of Congo Red, Thioflavin T, and Thioflavin S) include, e.g., [$^{11}$C]PIB, [$^{123}$I]IBOX (Zhuang, Kung et al. 2001. 28: 887-94), [$^{123}$I]IMPY, [$^{18}$F]FDDNP, [$^{11}$C]SB-13, [$^{11}$C]-BF-227. Among these, [$^{18}$F]FDDNP, [$^{11}$C]PIB, [$^{11}$C]SB-13, [$^{11}$C]-BF-227, and [$^{11}$C]-AV-45 have been used in clinical studies in AD patients and age-matched normal elderly with PET.

In the development of new therapies for the brain diseases, blood-brain-barrier (BBB) is considered as a major obstacle for the use of drugs having a potential in the treatment of central nervous system (CNS) diseases. Generally, only lipophilic molecules of less than about 500 Dalton can pass through BBB, i.e., from blood to brain. The above-mentioned PET imaging agents are all based on small chemical molecules. For passing through BBB, these small molecules should be lipo-soluble so as to pass through BBB in a passive diffusion way. However, the increased lipophilicity is always accompanied with increased non-specific binding. Thus, there is a need for an amyloid imaging agent avoiding small chemical molecule structure and passive diffusion manner, which is meaningful.

It has been reported that, angiopep-2, which is a ligand for low density lipoprotein receptor-related protein (LRP), shows higher efficiency in passing through BBB than brain-targeted groups such as transferrin. More importantly, LRP is not only expressed in brain capillary vessels endothelial cells, but also in amyloid deposits. As known in the prior art, angiopep-2, as a targeting group, can effectively improve the passing efficiency of drugs (e.g., ANG1005 from Angiochem) into intact BBB, and good therapeutic effects can be obtained. Thus, imaging agents labeled with angiopep-2 are promising in passing through BBB via a receptor-mediated action and obtaining the targeted labeling of the amyloid deposits in brain.

Up to now, it has not been reported that angiopep-2 can be used as both a BBB crossing agent and an amyloid deposit targeting agent, or amyloid deposit imaging agents labeled with imaging groups.

DISCLOSURE

The object of the present application is to overcome the deficiencies in the prior art, and to provide a novel polypeptide-based drug which can target amyloid deposits and can be used for the imaging and diagnosis of amyloid deposits. In particular, the present application relates to imaging drugs labeled with imaging groups which are capable of passing through the BBB and binding to amyloid deposits, and thus can be used for non-invasive tracing of amyloid deposits, especially when the BBB is intact.

Specifically, the present application relates to the followings:

1. A conjugate of formula R-L-M, wherein R is angiopep-2, L is a linker or chemical bond, and M is an optical imaging group, radioactive isotope, or an imaging group suitable for MRI or CT detection.

2. The conjugate according to item 1, wherein the angiopep-2 has a sequence of TFFYGGSRGKRNNFKTEEY (SEQ ID NO: 1).

3. The conjugate according to item 1, wherein the optical imaging group is FITC, Cy5.5, or a fluorescent protein.

4. The conjugate according to item 1, wherein the radioactive isotope is 99mTc, 123I, 125I, 131I, 11C, 13N, 15O, 18F, 22Na, 52Fe, 64Cu, 68Ga, 76Br, or 82Rb.

5. The conjugate according to 1, wherein the imaging group suitable for MRI detection is 19F, 13C, 15N, Mn2+, Gd3+, Dy3+, Fe2+, Fe3+ element or nano-iron, Gd-DTPA, Gd-DOPA, Mn-DPDP, iron oxide particle, transferrin, porphyrin compound or metal chelate.

6. The conjugate according to item 1, wherein the imaging group suitable for CT detection is iodine atom or nano-gold particle.

7. A drug or imaging agent comprising the conjugate of item 1 or the pharmaceutically acceptable salts thereof.

8. A method for targeting amyloid deposits, using the conjugate of item 1 or angiopep-2 as a targeting agent 9. A use imaging and diagnosis of amyloid-related diseases, for monitoring the proceeding of the diseases, for observing the therapeutic effects of drugs targeting the amyloid deposits, for the diagnosis, disease monitoring, and therapeutic effect evaluation in the animal model of amyloid diseases, which method comprising the administration of the conjugate of item 1 into a subject in need thereof.

10. The method according to item 9, wherein the amyloid-related diseases include Alzheimer's disease, type II diabetes, vessel amyloid deposition, and hereditary cerebral hemorrhage with amyloidosis.

Specifically, in the first aspect, the present application provides a polypeptide-based conjugate which can be used as a diagnostic imaging agent for targeting and tracing amyloid deposits, wherein angiopep-2 is used as both a BBB crossing group and an amyloid-targeting group. The imaging group on the conjugate enables the labeling and imaging of amyloid deposits, and thus diagnosing and tracing amyloid-related diseases such as Alzheimer's disease, and the proceeding thereof.

In a preferred embodiment, a pharmaceutical composition is administrated to individuals intraarterially, intranasally, intraperitoneally, intravenously, intramuscularly, subcutaneously, transdermally, or orally.

In a preferred embodiment, the administration comprises the step of: administrating to a patient an effective amount of the conjugate and/or a mixture comprising the conjugate and pharmaceutically acceptable carriers.

In a preferred embodiment, there is provided a conjugate of formula R-L-M or the pharmaceutically acceptable salts thereof, wherein R is angiopep-2, L is a linker or chemical bond, and M is selected from suitable optical imaging groups, radioactive isotopes or imaging groups suitable for MRI or CT detection.

In a preferred embodiment, the radioactive labels are suitable for PET (positron emission tomography) or SPECT (single-photon emission computed tomography) detection, and the radioactive isotopes include $^{99}$mTc, $^{123}$I, $^{125}$I, $^{131}$I, $^{11}$C, $^{13}$N, $^{15}$O, $^{18}$F, $^{22}$Na, $^{52}$Fe, $^{64}$Cu, $^{68}$Ga, $^{76}$Br, $^{82}$Rb.

In a preferred embodiment, the imaging groups suitable for MRI detection include: $^{19}$F, $^{13}$C, $^{15}$N, $Mn^{2+}$, $Gd^{3+}$, $Dy^{3+}$, $Fe^{2+}$, $Fe^{3+}$ element or nano-iron, Gd-DTPA, Gd-DOPA, Mn-DPDP, iron oxide particles, transferrin, porphyrin compounds or metal chelates.

In a preferred embodiment, the imaging groups suitable for CT detection include: iodine atom and nano-gold particle.

In a preferred embodiment, the imaging groups suitable for optical detection include: FITC, Cy5.5, fluorescent proteins, and the like.

In the second aspect, the present application provides a drug comprising the conjugate or the pharmaceutically acceptable salts thereof according to the first aspect of the present application.

In the third aspect, the present application provides a method for targeting amyloid deposits by using the conjugate according to the first aspect of the present application as a targeting agent.

In the fourth aspect, the present application provides a use of the conjugate according to the first aspect of the present application for the manufacture of drugs or kit for the imaging and diagnosis of amyloid-related diseases, for monitoring the proceeding of the diseases, for observing the therapeutic effects of drugs targeting amyloid deposits.

In a preferred embodiment, the amyloid-related diseases include: Alzheimer's disease, Down's syndrome, Type II diabetes, vessel amyloid deposits, amyloid polyneuropathy, amyloid myocardiopathy, systemic senile amyloid disease, hereditary cerebral hemorrhage with amyloidosis, and the like.

In a preferred embodiment, the conjugate and method of the present application can be applied in artificial animal model of amyloid-related diseases, including transgenic animals, knockout animals, such as APP transgenic mouse.

In a preferred embodiment, the vector and vector-drug conjugate of the present application can be used in combination with or separately from conventional treatment methods and/or therapies.

In a preferred embodiment, when the vector-imaging group conjugate of the present application is used in combination with other agents, they can be administrated to individuals sequentially or simultaneously. Alternatively, as described herein, the drug conjugate of the present application may consist of the combination of a pharmaceutically acceptable excipient and the vector-imaging group conjugate of the present application binding to another treating or imaging agent known in the art.

It will be appreciated that, a certain "effective amount" for a certain individual will depend on many factors including the activity of the specific drug used, the age, weight, general health, gender and/or diet of the individual, the timing and route of administration, excretion rate, drug combination, and the severity of the diseases to be prevented or treated.

Pharmaceutically acceptable acid addition salts can be produced by methods well-known in the art.

As used herein, "pharmaceutically acceptable carriers" include any and all of solvents (such as PBS, water, saline), dispersing agents, coating agents, antibacterial agents and antifungal agents, isotonizing agents and absorption delaying agents, and the like. These media and agents are well-known in the art for their use with pharmaceutically active substances. The use of any conventional medium or agent in the treatment composition may be contemplated, unless incompatible with active gradients. Additional active gradients can also be added into the compositions.

The term "derivatives" refers to "chemical derivatives", "fragments" or "variant" biologically active sequences or parts of the vector or vector-imaging group conjugate of the present application or the salts thereof. The vector derivatives may be linked to or conjugated with another compound or agent, passing through BBB, and thus enable the transport of other compounds or agents through BBB and binding to amyloid deposits.

The term "chemical derivatives" refers to the vector or vector-imaging group conjugate of the present application, which comprises additional chemical moieties that are not part of the vector or vector-imaging group conjugate. Covalent modifications are also included in the scope of the present application. The chemical derivatives can be produced through direct chemical synthesis by using methods well-known in the art. These modifications may be, e.g., reaction of an amino acid residue of interest with organic derivation agents which can react with selected side chains or terminal residues, introduction into a protein or peptide vector or vector-imaging group conjugate. The vector chemical derivatives can pass through BBB and can be linked to or conjugated with another compound or agent, and thus enable the transport of another compound or agent through BBB and binding to amyloid deposits.

EMBODIMENTS

The following examples are provided for better understanding the present application, rather than limiting the scope of the present application.

In following examples, angiopep-2 was purchased from GL Biochem (Shanghai) Ltd., FITC, Thioflavin S, and Aβ1-42 were purchased from Sigma-Aldrich (China), Cy5.5-NHS was purchased from Heowns Biochem Technologies LLC. Other common reagents were purchased from Sinopharm Chemical Reagent Co. Ltd, unless otherwise indicated. APP mice were purchased from Nanjing Biomedical Research Institute of Nanjing University. Paraffin human AD brain issues were obtained from Ethical Committee of the Medical Faculty of the Free University (VUMC, Amsterdam, The Netherlands, 971019).

Example 1: The Preparation of a Conjugate Formed by Angiopep-2 and FITC

1. Fmoc-Tyr(tbu)-wang resin was soaked in DMF for 30 minutes.

2. Decapping: decapping with 20% hexahydropyridine/80DMF for 30 minutes, then washing with DMF for 6 times, reaction in 3-fold amount of Fmoc-Glu(otbu)-oh, HBTU, NMM, DMF solution for 30 minutes.

3. Washing with DMF for three times, taking a small amount of the resin and heating in detection solution (ninhydrin, phenol, pyridine, two drops for each) at 120° C. for 3 minutes; reaction endpoint: colorless and transparent.

4. Repeating steps 2 and 3, reaction with Fmoc-Glu(otbu)-oh, Fmoc-Thr(tbu), Lys(boc)-oh, Fmoc-Phe-oh, Fmoc-Asn(trt)-oh, Fmoc-Asn(trt)-oh, Fmoc-Arg(pbf)-oh, Fmoc-Lys(boc)-oh, Fmoc-Gly-oh, Fmoc-Arg(pbf)-oh, Fmoc-Ser(tbu)-oh, Fmoc-Gly-Gly-oh, Fmoc-Tyr(tbu)-oh, Fmoc-Phe-oh, Fmoc-Phe-oh, Fmoc-Thr(tbu), Fmoc-Acp-oh, and 5-Fitc.

5. Washing with methanol and DCM alternately for 3 times, then again with methanol for 2 times, removing residual methanol, and weighing the resin.

6. Cutting: adding cutting fluid (87.5% TFA/2.5% $H_2O$/2.5EDT/2.5 phenol/5% thioanisole) to the treated resin (10 mg of cutting fluid for 1 g of resin); reacting for 2 hours; after reaction completion, filtrating; adding 5-fold amount of ether to the filtrate for precipitating solid.

7. Centrifuging and drying, affording crude solid; purifying by prep-HPLC.

Figure 1:
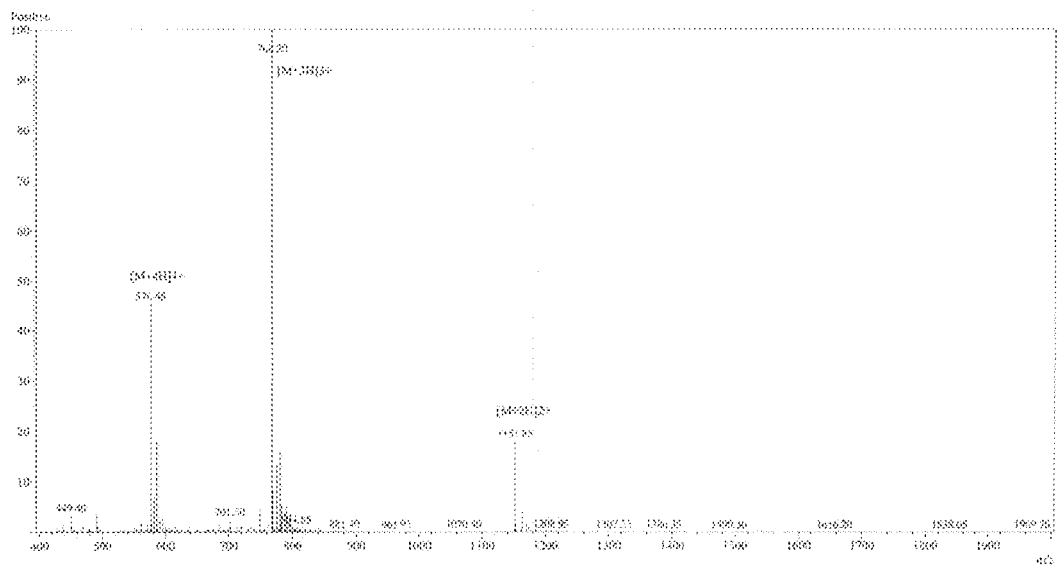
FIG. 1. The ESI-MS spectrum of angiopep-2, the sequence of the polypeptide: TFFYGGSRGKRNNFK-TEEY, MW: 2301.52 Da (SEQ ID NO: 1).
Figure 2:
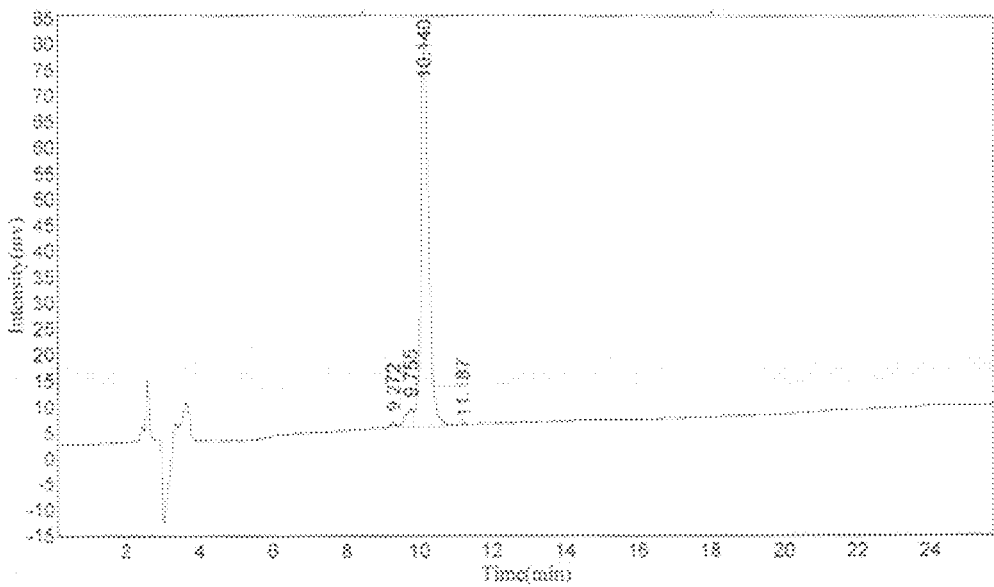
FIG. 2. The HPLC spectrum of angiopep-2: chromatography method: chromatographic column: Venusil MP C18-5 HPLC COLUMN 250×4.6 mm; mobile phase A: 0.1% aqueous solution of TFA; mobile phase B: 0.1% aqueous TFA solution; flow rate: 1 mL/min; time: 30 minutes; detection at 220; eluting procedure: from 0.01 to 25 minutes, linear elution of from 85% B to 60% B, and finally, washing the column with 0% B to 30 minutes.
Figure 3:
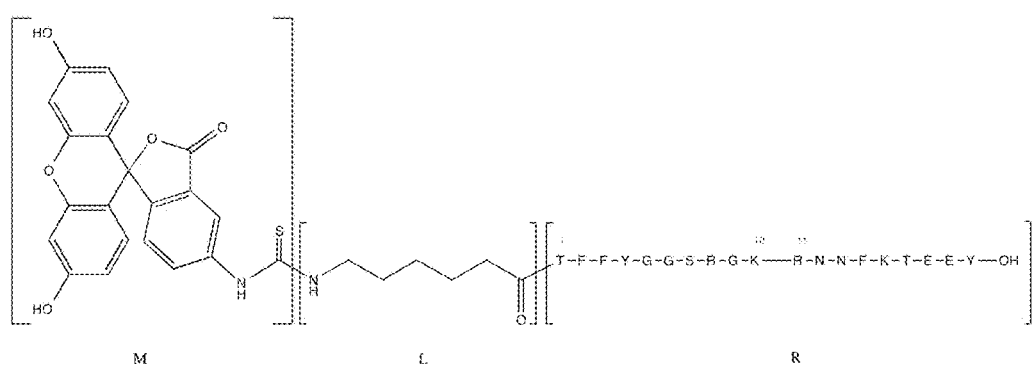
FIG. 3. The structure of a conjugate formed by angiopep-2 and FITC.
Figure 5:
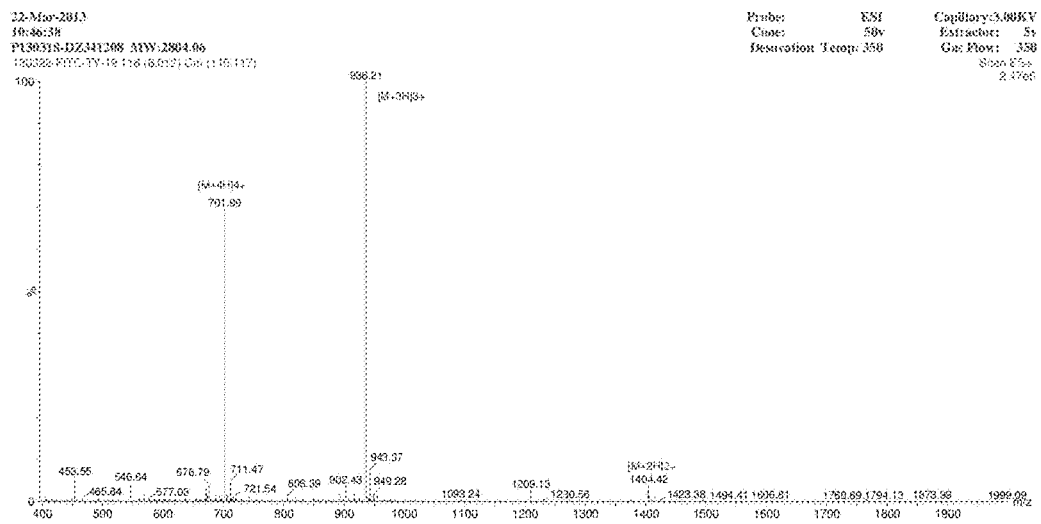
FIG. 5. The ESI-MS spectrum of the conjugate formed by angiopep-2 and FITC, MW: 2804.06 Da FIG. 6. The HPLC spectrum of the conjugate formed by angiopep-2 and FITC, chromatography method: chromatographic column: VYDAC-C18HPLC COLUMN 250×4.6 mm; mobile phase A: acetonitrile solution; mobile phase B: 0.01M aqueous solution of phosphoric acid; flow rate: 1 mL/min; time: 30 minutes; detection at 220; eluting procedure: from 0.01 to 25 minutes, linear elution of from 85% B to 40% B, and finally, washing the column with 0% B to 30 minutes.
Figure 6:
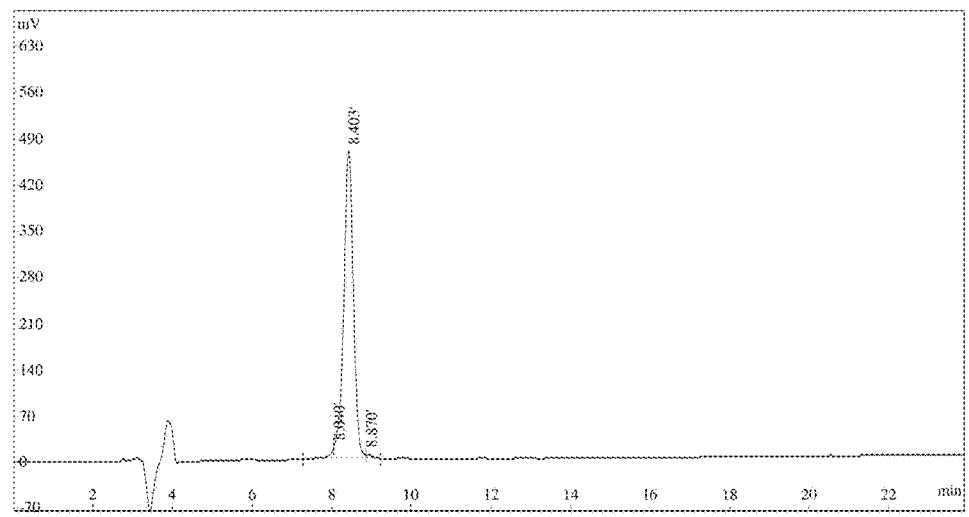

8. Sample analysis by MS and analytical HPLC. See FIGS. 1 and 2 for the MS and HPLC spectra of angiopep-2 moiety. See FIG. 3 for the schematic view of the structure of the conjugate formed by angiopep-2 and FITC. See FIGS. 5 and 6 for the MS and HPLC spectra of the conjugate formed by angiopep-2 and FITC.

The Figures demonstrate right synthesis of angiopep-2 and the conjugate formed by angiopep-2 and FITC.

Example 2: The Preparation of a Conjugate Formed by Angiopep-2 and Cy5.5

Figure 4:
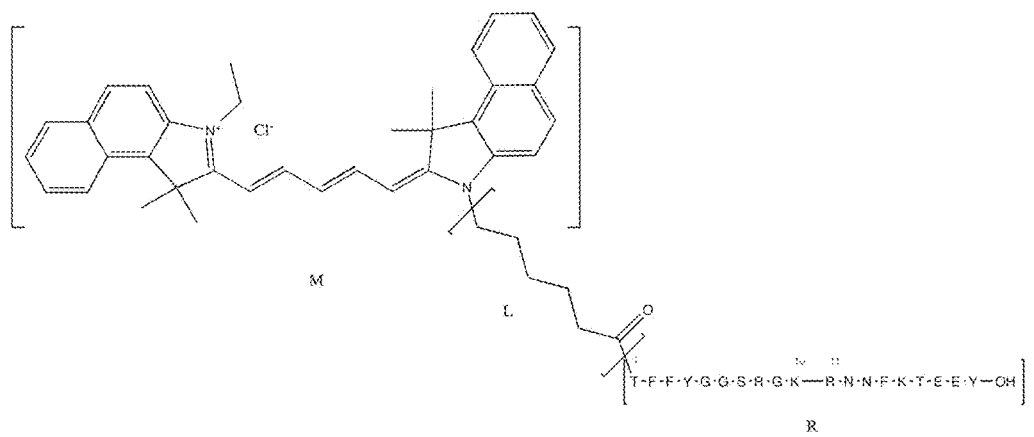
FIG. 4. The structure of a conjugate formed by angiopep-2 and Cy5.5.
Figure 7:
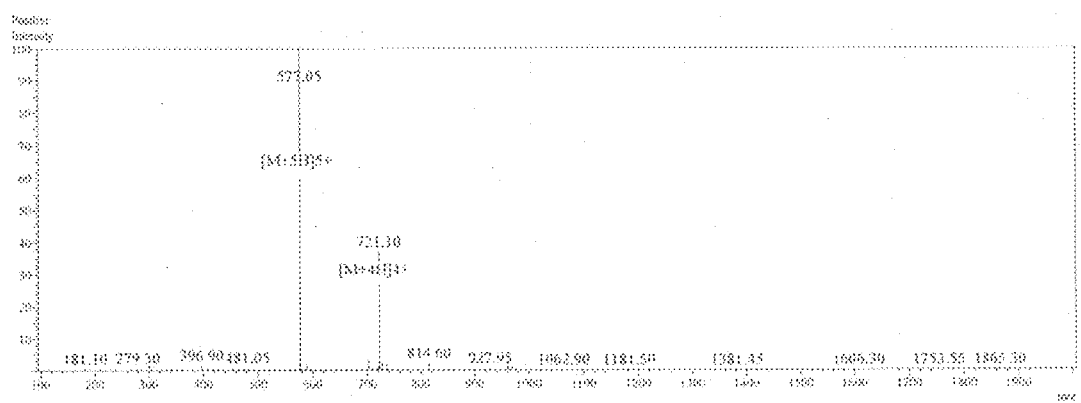
FIG. 7. The ESI-MS spectrum of the conjugate formed by angiopep-2 and Cy5.5, MW: 2880.24 Da.
Figure 8:
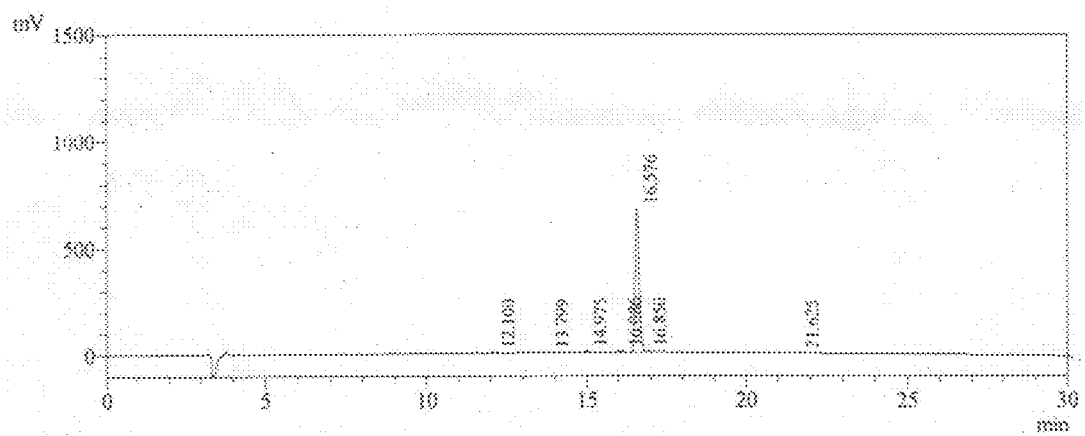
FIG. 8. The HPLC spectrum of the conjugate formed by angiopep-2 and Cy5.5, chromatography method: chromatographic column: SHIMADZU Inertsil ODS-SP HPLC COLUMN 250×4.6 mm; mobile phase A: 0.1% aqueous solution of TFA; mobile phase B: 0.1% aqueous solution of TFA: flow rate: 1 mL/min; time: 40 minutes; detection at 214; eluting procedure: from 0.01 to 30 minutes, linear elution of from 30% B to 95% B, from 30 to 33 minutes, linear elution of from 95% B to 100% B, and finally, washing the column with 0% B to 40 minutes.

1. Fmoc-Tyr(tbu)-wang resin was soaked in DMF for 30 minutes.
2. Decapping: decapping with 20% hexahydropyridine/80DMF for 30 minutes, then washing with DMF for 6 times, reaction in 3-fold amount of Fmoc-Glu(otbu)-oh, HBTU, NMM, DMF solution for 30 minutes.
3. Washing with DMF for three times, taking a small amount of the resin and heating in detection solution (ninhydrin, phenol, pyridine, two drops for each) at 120° C. for 3 minutes; reaction endpoint: colorless and transparent.
4. Repeating steps 2 and 3, reaction with Fmoc-Glu(otbu)-oh, Fmoc-Thr(tbu). Lys(boc)-oh, Fmoc-Phe-oh, Fmoc-Asn(trt)-oh, Fmoc-Asn(trt)-oh, Fmoc-Arg(pbf)-oh, Fmoc-Lys(boc)-oh, Fmoc-Gly-oh, Fmoc-Arg(pbf)-oh, Fmoc-Ser(tbu)-oh, Fmoc-Gly-Gly-oh, Fmoc-Tyr(tbu)-oh, Fmoc-Phe-oh, Fmoc-Phe-oh, Fmoc-Thr(tbu), Fmoc-Acp-oh, and Cy5.5-NHS.
5. Washing with methanol and DCM alternately for 3 times, then again with methanol for 2 times, removing residual methanol, and weighing the resin.
6. Cutting: adding cutting fluid (87.5% TFA/2.5% $H_2O$/2.5EDT/2.5 phenol/5% thioanisole) to the treated resin (10 mg of cutting fluid for 1 g of resin); reacting for 2 hours; after reaction completion, filtrating; adding 5-fold amount of ether to the filtrate for precipitating solid.
7. Centrifuging and drying, affording crude solid; purifying by prep-HPLC.
8. Sample analysis by MS and analytical HPLC. See FIG. 4 for the schematic view of the structure of the conjugate formed by angiopep-2 and Cy5.5. See FIGS. 7 and 8 for the MS and HPLC spectra of the conjugate formed by angiopep-2 and FITC.

The Figures demonstrate right synthesis of angiopep-2 and the conjugate formed by angiopep-2 and Cy5.5.

Example 3: Fluorescent Staining of AD Patients' Brain Sections Labeled with the Conjugate Formed by Angiopep-2 and FITC Comparative stainings were performed on a series of AD patients' brain sections as follows:
1. Dewaxing to water: xylene I for 10 minutes; xylene II for 10 minutes; 100% ethanol I for 10 minutes; 100% ethanol II for 10 minutes; 95% ethanol for 5 minutes, 90% ethanol for 5 minutes, 80% ethanol for 5 minutes, 70% ethanol for 5 minutes, washing with ultrapure water for 5 seconds and twice with PBS (Ph7.4) for 5 minutes.
2. Treating with potassium permanganate solution (0.25% in PBS) for 20 minutes (until the sections turning into brown), 3 times with PBS for 2 minutes; treating the sections with a mixture solution of potassium metabisulfite (1.0% in PBS) and oxalic acid (1.0% in PBS) until brown color fades (for about 1-6 minutes, the treatment continuing for 30 seconds after the fading of brown color of the sections), 3 times with PBS for 2 minutes.
3. Drawing circles with Pap pen. The sections of the conjugate formed by angiopep-2 and FITC and the sections of Thioflavin S were stained respectively as follows:
Staining for the conjugate formed by angiopep-2 and FITC: (following step 3 above)
4. Staining with 300 ul solution of the conjugate formed by angiopep-2 and FITC (0.1 mM) by drops, in wet box at 37° C. for 1 h.
5. Washing twice with PBS for 10 minutes.
6. Mounting with 70% glycerin, storing at 4° C.
Staining with Thioflavin S: (following step 3 above)
7. Thioflavin S (0.5 g % in PBS), staining for 20 minutes (by drops).
8. Treating with 70% ethanol for 10 minutes, and with PBS for 5 minutes.
9. Mounting with 80% glycerin.

Figure 9:
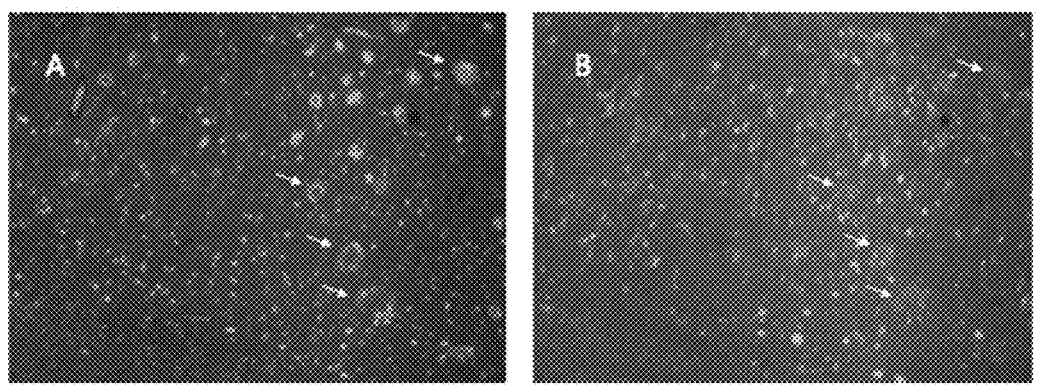
FIG. 9. The photographs of fluorescent staining of AD patients' brain sections labeled with the conjugate formed by angiopep-2 and FITC.

The results are shown in FIG. 9. FIG. 9A shows the photograph of the staining with the conjugate formed by angiopep-2 and FITC, and FIG. 9B shows the photograph of the staining with positive control Thioflavin S. White arrows indicate amyloid deposits. This Figure demonstrates that the conjugate formed by angiopep-2 and FITC can bind to the amyloid deposits in AD patients' brain sections.

Example 4: Fluorescent Staining of APP Transgenic Mouse's Brain Sections Labeled with the Conjugate Formed by Angiopep-2 and FITC Comparative stainings were performed on a series of APP transgenic mouse's brain sections as follows:
1. Washing twice with PBS (Ph7.4) for 5 minutes.
2. Treating with potassium permanganate solution (0.25% in PBS) for 20 minutes (until the sections turning into brown), 3 times with PBS for 2 minutes; treating the sections with a mixture solution of potassium metabisulfite (1.0% in PBS) and oxalic acid (1.0% in PBS) until brown color fades (for about 1-6 minutes, the treatment continuing for 30 seconds after the fading of brown color of the sections), 3 times with PBS for 2 minutes.
3. Drawing circles with Pap pen. The sections of the conjugate formed by angiopep-2 and FITC and the sections of Thioflavin S were stained respectively as follows:
Staining for the conjugate formed by angiopep-2 and FITC: (following step 3 above)
4. Staining with 300 ul solution of the conjugate formed by angiopep-2 and FITC (0.1 mM) by drops, in wet box at 37° C. for 1 h.
5. Washing twice with PBS for 10 minutes.
6. Mounting with 70% glycerin, storing at 4° C.
Staining with Thioflavin S: (following step 3 above)
7. Thioflavin S (0.5 g % in PBS), staining for 20 minutes (by drops).
8. Treating with 70% ethanol for 10 minutes, and with PBS for 5 minutes.
9. Mounting with 80% glycerin.

Figure 10:
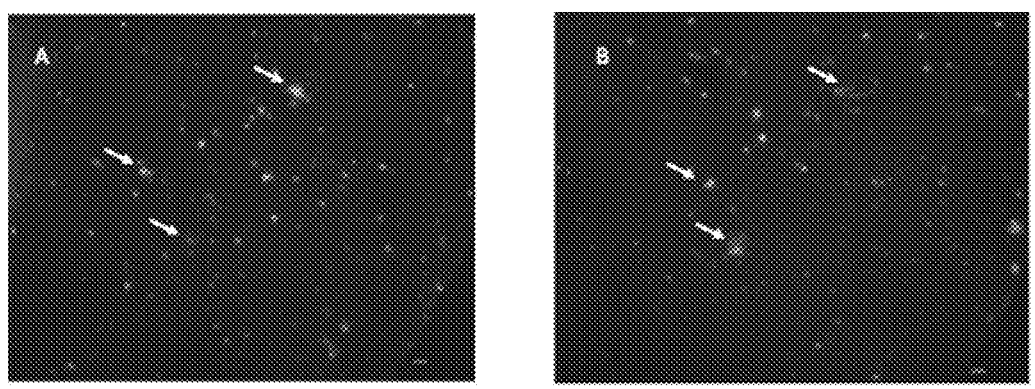
FIG. 10. The photographs of fluorescent staining of APP transgenic mouse's brain sections labeled with the conjugate formed by angiopep-2 and FITC.

The results are shown in FIG. 10. FIG. 10A shows the photograph of the staining with the conjugate formed by angiopep-2 and FITC, and FIG. 10B shows the photograph of the staining with positive control Thioflavin S. White arrows indicate amyloid deposits. This Figure demonstrates that the conjugate formed by angiopep-2 and FITC can bind to the amyloid deposits in APP transgenic mouse's brain sections.

Example 5: Interaction Between the Conjugate Formed by Angiopep-2 and FITC and Aβ1-42

1. Dissolving Aβ1-42 solid in PBS (PH 7.4) at a concentration of 0.25 mg/ml (55.38 uM), incubating in 37° C. water bath on a shaker for 42 h.

2. Preparing solutions (containing 10% DMF), containing the conjugate formed by angiopep-2 and FITC (10 uM) as well as Aβ1-42 aggregates (0, 5, 10 uM) or BSA (45 ug/mL), respectively; incubating the mixture solution at 37° C. for 30 minutes.

3. Preparing solutions (containing 10% DMF), containing the conjugate formed by angiopep-2 and FITC (0-3.75 uM) as well as Aβ1-42 aggregates (2.2 uM) or BSA (10 uM), respectively, incubating the mixture solution at 37° C. for 30 minutes.

4. Detecting the mixture solutions prepared above for their emission spectrum with fluorescence spectrophotometer, emission wavelength: 333 nm, maximum emission wavelength: 531 nm, in the range of 500-600 nm.

5. Plotting by using GraphPad Prism 5.0 (GraphPad Software, Inc., La Jolla, Calif., USA) and calculating equilibrium dissociation constant.

Figure 11:
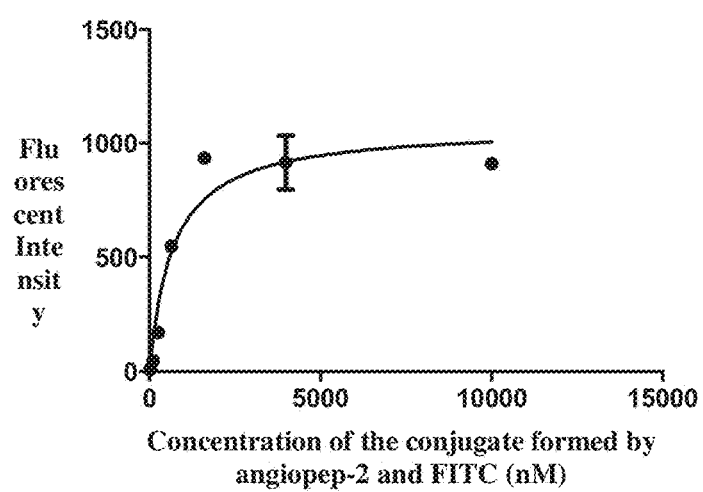
FIG. 11. The profile of the interaction between the conjugate formed by angiopep-2 and FITC and Aβ1-42, showing the affinity of the conjugate to Aβ1-40.

As shown in FIG. 11, the conjugates formed by angiopep-2 and FITC interacted with Aβ1-42 in a saturation-curve manner. As calculated, the equilibrium dissociation constant is 676.3 nM. It was demonstrated that, the conjugates can interact with and bind to Aβ1-42 in a saturation-curve manner.

Example 6: Fluorescent Microscopy Observation of APP Transgenic Mouse's Brain Sections after Administration of the Conjugate Formed by Angiopep-2 and FITC by Intravenous Injection An APP transgenic mouse was anaesthetized with pentobarbital sodium (80 mg/kg), and injected with the conjugate formed by angiopep-2 and FITC at 23 mg/kg by tail vein injection. After 30 minutes, the mice were sacrificed, and then their brains were removed and frozen in liquid nitrogen. Major organs including heart, liver, spleen, lung, kidney and muscles were removed and subjected to fluorescent screening (IVIS imaging system, an optical imaging system from Caliper Life Sciences for imaging living body). The brain was cut into sections of about 25 m in thickness using a frozen tissue microtome (Lecia CM1950). The sections were then placed on a fluorescent microscope (IX8, OLYMPUS) for observation and photography.

Figure 12:
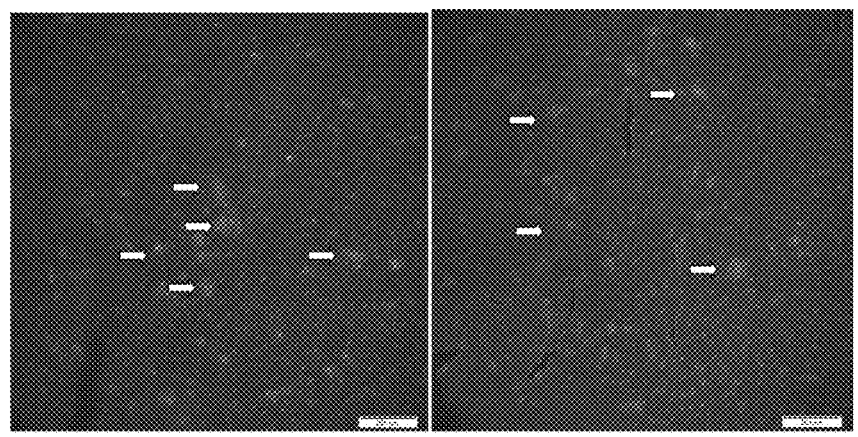
FIG. 12. The photographs of fluorescent microscopy of APP transgenic mouse's brain sections after administration of the conjugate formed by angiopep-2 and FITC by intravenous injection.

The results are shown in FIG. 12. The white arrows in the Figure indicate the amyloid deposits. This Figure demonstrates that the conjugate formed by angiopep-2 and FITC can bind to and label the amyloid deposits in the sections of an APP transgenic mouse in vivo.

Example 7: In Vivo Near-Infrared Imaging of APP Transgenic Mouse after Administration of the Conjugate Formed by Angiopep-2 and Cy5.5 by Intravenous Injection Optical in vivo imaging study was performed on IVIS imaging system, an optical imaging system from Caliper Life Sciences for imaging living body with an excitation filter set as Cy5.5, and emission spectrum band-pass filter as 640 nm. Before imaging, the mice were anaesthetized with a mixture gas of isoflurane and oxygen, and placed on an imaging plate with its face downward. White light photography (exposure time: 0.2 s) and near-infrared fluorescent imaging (exposure time: 5 s) were performed under the same field of vision (FOV) (FOV=12.5 cm, f/stop=1, Bin=1) at time points including before injection and several selected time points after intravenous injection. Each mouse received an injection dose of 13 mg/kg. White light photographs and near-infrared fluorescent images were superimposed to determine the size of intracranial portion. Finally, the imaging views were processed by using Living Image Software (Caliper Life Sciences).

Figure 13:
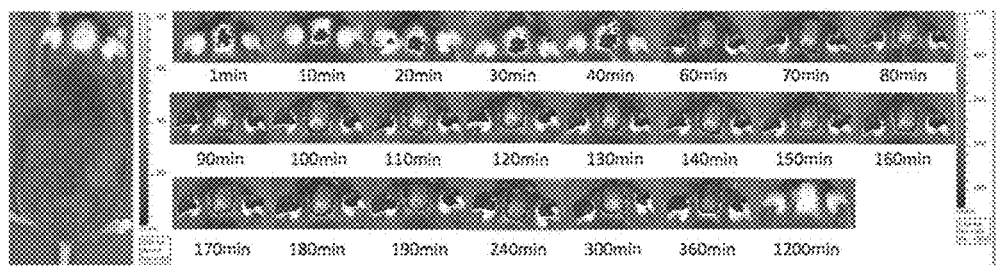
FIG. 13. The photographs of in vivo near-infrared imaging of APP transgenic mouse's brain sections after administration of the conjugate formed by angiopep-2 and Cy5.5 by intravenous injection.

As shown in FIG. 13, the conjugates formed by angiopep-2 and Cy5.5 aggregated in APP mice's brains, and after 20 hours, were cleared. This Figure demonstrates that the conjugate formed by angiopep-2 and FITC can pass through BBB and aggregate in APP transgenic mice's brains in vivo.

Example 8: Fluorescent Microscopy Observation of APP Transgenic Mouse's Brain Sections after Administration of the Conjugate Formed by Angiopep-2 and Cy5.5 by Intravenous Injection 30 minutes after intravenous administration (13 mg/kg), the mice were sacrificed, and then their brains were removed and frozen in liquid nitrogen. Major organs including heart, liver, spleen, lung, kidney and muscles were removed and subjected to fluorescent screening. The brain was cut into sections of about 25 m in thickness using a frozen tissue microtome (Lecia CM1950). The sections were then placed on a fluorescent microscope (IX8, OLYMPUS) for observation and photography.

Figure 14:
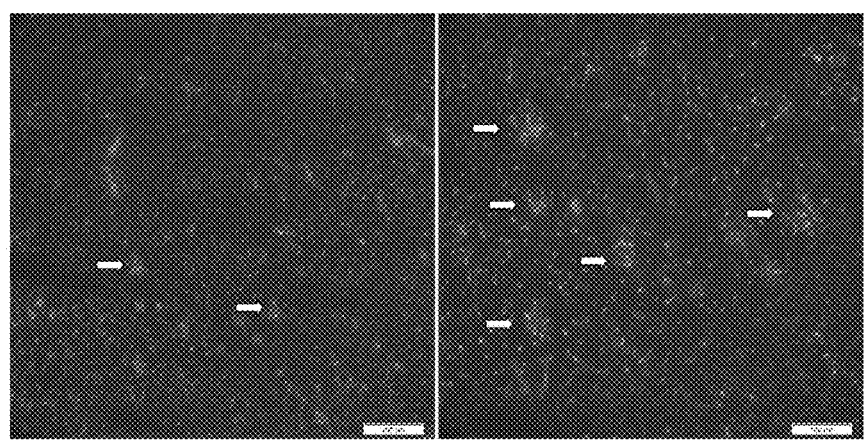
FIG. 14. The photographs of fluorescent microscopy of APP transgenic mouse's brain sections after administration of the conjugate formed by angiopep-2 and Cy5.5 by intravenous injection.

The results are shown in FIG. 14. The white arrows in the Figure indicate amyloid deposits. This Figure demonstrates that the conjugate formed by angiopep-2 and Cy5.5 can bind to and label the amyloid deposits in the brain sections of an APP transgenic mouse in vivo.

We claim:

1. A method of targeting amyloid deposits comprising contacting a targeting agent of formula R-L-M,
   wherein R is angiopep-2, L is a linker or a chemical bond, and M is an optical imaging group, a radioactive isotope, or an imaging group suitable for MRI or CT detection;
   wherein the imaging group suitable for MRI detection is 19F, 13C, 15N, Mn2+, Gd3+, Dy3+, Fe2+, Fe3+, element or nano-iron, Gd-DTPA, Gd-DOPA, Mn-DPDP, iron oxide particle, transferrin, porphyrin compound or metal chelate;
   wherein the imaging group suitable of CT detection is iodine atom or nano-gold particle; and
   with tissue and allowing targeting agent to bind to amyloid deposits in the tissue,
   wherein the angiopep-2 has a sequence of TFFYGGSRG-KRNNFKTEEY (SEQ ID NO:1).

2. A method of imaging and diagnosing an amyloid-related disease comprising administering a targeting agent of formula R-L-M
   wherein R is angiopep-2, L is a linker or a chemical bond, and M is an optical imaging group, a radioactive isotope, or an imaging group suitable for MRI or CT detection;
   wherein the imaging group suitable for MRI detection is 19F, 13C, 15N, Mn2+, Gd3+, Dy3+, Fe2+, Fe3+ element or nano-iron, Gd-DTPA, Gd-DOPA, Mn-DPDP, iron oxide particle, transferrin, porphyrin compound or metal chelate;
   wherein the imaging group suitable for CT detection is iodine atom or nano-gold particle;
   to tissue and allowing the targeting agent to bind to amyloid deposits in the tissue
   wherein angiopep-2 has a sequence of TFFYGGSRG-KRNNFKTEEY (SEQ ID NO:1) and
   wherein the amyloid-related disease is selected from the group consisting of Alzheimer's disease, type II diabetes, vessel amyloid deposits, and hereditary cerebral hemorrhage with amyloidosis.

3. The method according claim 1, wherein the optical imaging group is FITC, Cy5.5, or a fluorescent protein.

4. The method according claim 1, wherein the radioactive isotope is $^{99m}$Tc, $^{123}$I, $^{125}$I, $^{131}$I, $^{11}$C, $^{13}$N, $^{15}$O, $^{18}$F, $^{22}$Na, $^{52}$Fe, $^{64}$Cu, $^{68}$Ga, $^{76}$Br, or $^{82}$Rb.

* * * * *